United States Patent
Omary et al.

(10) Patent No.: US 8,343,260 B2
(45) Date of Patent: *Jan. 1, 2013

(54) FLUORINATED METAL-ORGANIC FRAMEWORKS FOR GAS STORAGE

(75) Inventors: Mohammad A. Omary, Denton, TX (US); Chi Yang, Denton, TX (US)

(73) Assignee: University of North Texas, Denton, TX (US)

( * ) Notice: Subject to any disclaimer, the term of this patent is extended or adjusted under 35 U.S.C. 154(b) by 282 days.

This patent is subject to a terminal disclaimer.

(21) Appl. No.: 12/676,555

(22) PCT Filed: Sep. 12, 2008

(86) PCT No.: PCT/US2008/010664
§ 371 (c)(1),
(2), (4) Date: Jun. 22, 2010

(87) PCT Pub. No.: WO2009/035664
PCT Pub. Date: Mar. 19, 2009

(65) Prior Publication Data
US 2010/0282080 A1    Nov. 11, 2010

Related U.S. Application Data

(60) Provisional application No. 60/993,844, filed on Sep. 14, 2007.

(51) Int. Cl.
*C07F 1/10* (2006.01)
*B01J 20/22* (2006.01)
(52) U.S. Cl. .............................. 95/116; 95/147; 548/101
(58) Field of Classification Search .................... 96/108; 95/90, 116, 129, 130, 138–147, 900; 206/0.7; 502/400, 526; 548/101
See application file for complete search history.

(56) References Cited

U.S. PATENT DOCUMENTS

| 7,553,352 B2 * | 6/2009 | Mueller et al. .................. 95/90 |
| 7,910,732 B2 * | 3/2011 | Schubert et al. .............. 544/226 |
| 2010/0132549 A1 * | 6/2010 | Yaghi et al. ..................... 95/128 |

OTHER PUBLICATIONS

Yang G et al: "A Robust, Porous, Cationic Silver(I) 3,5-Dipenyl-1,2,4-Triazolate Framework with a Uninodal 4<9>.6<6> Net" Chemical Communications, Royal Society of Chemistry, GB, vol. 10, No. 18, Jan. 2004, pp. 2058-2059.*
Abdul-Ghani, M.M., et al; Unsaturated Nitrogen Compounds Containing Fluorine; J. Fluo. Chem. 1995, 72, 95-106.
Dinca, M., et al., Hydrogen Storage in a Microporous Metal-Organic Framework With Exposed MN2+ Coordination Sites; J. Am. Chem. Soc. 2006, 128, 16876-16883.
Ouellette, W., et al; Hydrothermal Chemistry of the Copper-Triazolate System, J. Angew. Chem. Int. Ed. 2006, 45, 3497-3500.
Spek, A. L.; Single-Crystal Structure Validation With the Program Platon; J. Appl. Crystallogr. 2003, 36, 7-13.
Yaghi, O. M., et al; Selective Binding and Removal of Guests in a Microporous Metal-Organic Framework; Nature 1995, 378, 703-706.

(Continued)

*Primary Examiner* — Frank Lawrence, Jr.
(74) *Attorney, Agent, or Firm* — Jackson Walker L.L.P.

(57) ABSTRACT

Fluorinated metal-organic frameworks ("FMOFs") are capable of adsorbing and desorbing gases and molecules. The FMOFs can be arranged in a variety of configurations and have internal hollow channels and cavities. In the FMOFs, hydrogen atoms have been substituted completely or partially with fluorine atoms or fluorinated groups in each linking organic ligand. The FMOFs have high densities, leading to an enhanced volumetric capacity for gas storage.

17 Claims, 7 Drawing Sheets

OTHER PUBLICATIONS

Wong-Foy, A.G., et al.; Exceptional H2 Saturation Uptake in Microporous Metal-Organic Frameworks; J. Am. Chem. Soc. 2006, 128, 3494-3495.

Zhang, J. P., et al; Two Unprecedented 3-Connected Three-Dimensional Networks of Copper Triazolates; Angew. Chem. Int. Ed. 2004, 43, 206-209.

Zhang, J. P., et al; Copper(I) 1,2,4-Trizolates and Related Complexes; J. Am. Chem. Soc. 2005, 127, 5495-5506.

Zhang, J. P., et al; Temperature- or Guest-Induced Drastic Single-Crystal-To-Single-Crystal Transformations of a Nanoporous Coordination Polymer; J. Am. Chem. Soc. 2005, 127, 14162-14163.

European Patent Office; International Search Report and Written Opinion; PCT Application No. PCT/US2008/010664; Jan. 5, 2009.

European Patent Office; International Preliminary Report on Patentability; PCT Application No. PCT/US2008/010664; Dec. 15, 2009.

Yang, Chi, et al; Fluorous Metal-Organic Frameworks for High-Density Gas Adsorption; J. American Chem. Soc.; Dec. 19, 2007, 129, 50, 15454-15455.

Chen, et al; A Self-Assembled Porous Zn(II) Metal-Organic Framework Based on Fluorinated Bis-Pyridinecarboxamide Derivative Ligand; Inorganic Chemistry Communications, Mar. 7, 2007,10, 4, 451-454.

Fasina, T.M, et al; Synthesis, Optical Properties, Crystal Structures and Phase Behaviour . . . , J. Materials Chemistry, Aug. 7, 2004; 14, 15, 2395-2404.

Ferrer, M., et al; Equilibria Between Metallosupramolecular Squares and Triangles . . . , Inorganic Chemistry, Sep. 22, 2003, 42, 19, 5890-5899.

Kasai, K, et al; Flexible Coordination Networks With Fluorinated Backbones; J. American Chem. Soc., Mar. 8, 2000, 122, 9, 2140-2141.

Domasevitch, K.V., et al; Silver(1) Ions Bridged by Pyridazine: Doubling the Ligand Functionality for the Design of Unusual 3D Coordination Frameworks; Dalton Transactions 2007 Royal Soc. of Chem., Jun. 23, 2007, 3893-3905.

\* cited by examiner

FLUORINATED METAL-ORGANIC FRAMEWORKS FOR GAS STORAGE

This application claims priority to International Application No. PCT/US2008/010664, filed Sep. 12, 2008, entitled "FLUORINATED METAL-ORGANIC FRAMEWORKS FOR GAS STORAGE" which claims priority to U.S. Provisional Patent Application Ser. No. 60/993,844, entitled "FLUORINATED METAL-ORGANIC FRAMEWORKS FOR GAS STORAGE" filed on Sep. 14, 2007, the entire content of each of which is hereby incorporated by reference.

BACKGROUND

This invention pertains to fluorinated metal-organic frameworks having internal channels and cavities in a variety of configurations that are capable of adsorbing and desorbing gases and molecules. This invention also pertains to gas storage in fluorinated metal organic frameworks, and more particularly to hydrogen storage.

Crystalline porous materials, either with an inorganic or a metal-organic framework ("MOF"), can be used in a range of applications. These include size- and shape-selective catalysis, separations, gas storage, ion-exchange, sensors, and optoelectronics. In particular, stable MOFs with permanent highly-porous channels or cavities have been explored as effective, economic, and safe on-board vehicular gas (hydrogen or methane) storage materials for fuel-cell-driven automobiles. Extensive efforts have been devoted to the rational design and construction of new MOFs with zeolite-like, well-defined, stable and extra large micro or meso pore size channels exhibiting higher or selective gas affinity properties. Pioneered by Yaghi et al., a vast number of organic ligands with a variety of donor groups and over 40 metal cations have been explored in MOF construction (Yaghi, et al. 1995). A few reports on MOFs utilizing non-fluorinated metal triazolates have appeared recently. (Yang, et al. 2004; Zhang, et al. 2004, 2005; Ouellette 2006).

High volumetric capacity is a very significant property for gas storage applications. The U.S. Department of Energy ("DOE") has established a multi-stage target for hydrogen storage capacity in materials, including those materials intended for fuel cell applications. The DOE's 2010 targets for a hydrogen-storage system are an energy density of 7.2 MJ/kg and 5.4 MJ/L. Energy density refers to the amount of usable energy that can be derived from the fuel system. The figures include the weight and size of the container and other fuel-delivery components not just the fuel. The 2010 values work out to be 6 wt % of hydrogen and 45 kg of hydrogen per cubic meter. For 2015, the DOE is calling for fuel systems with 9 wt % of hydrogen and 81 kg of hydrogen per cubic meter, which is greater than the density of liquid hydrogen (approximately 70 kg/m$^3$ at 20 K and 1 atm). Particularly for $H_2$ storage in automobiles, the volumetric capacity is arguably more important than the gravimetric capacity because smaller heavy cylinders are easier to accommodate in vehicles than larger cylinders even if the latter were lighter than the former. Due to their high porosity, the best metal-organic frameworks known to date have very low densities (e.g., 0.43, 0.51, and 0.62) (Yaghi, et al. 2006; Long, et al. 2006). Therefore, their volumetric densities are always lower than the gravimetric densities.

In attempts to meet the DOE targets, nanostructured carbon materials (e.g. carbon nanotubes, graphite nanofibers, activated carbon, and graphite) and porous metal-organic frameworks have become of interest to researchers as potential hydrogen adsorbents. However, it has been shown that nanostructured carbons have slow uptake, exhibit irreversible adsorption, and contain reduced transition metals as impurities. Meanwhile, the known MOFs have low volumetric $H_2$ uptake due to their low densities and weak affinity to hydrogen molecules. In addition, the porous nature and high surface areas of metal-organic frameworks give rise to rather weak $H_2$ adsorption energies (~5 kJ/mol). This is why cryogenic temperatures are usually required to observe significant $H_2$ uptake.

What is needed, therefore, is a MOF that is stable and capable of adsorbing a high volume of gases at higher temperature.

SUMMARY

The present invention relates generally to fluorinated metal-organic frameworks ("FMOFs") having enhanced gas adsorption and desorption capacities. All ligands in the FMOFs contain fluorine atoms instead of some or all of the hydrogen atoms in each ligand. In a preferred embodiment, the present invention pertains to fluorous (i.e., perfluorinated) metal-organic frameworks, wherein all hydrogen atoms are substituted by fluorine atoms. Compared to their non-fluorinated counterparts, FMOFs with fluoro-lined or fluoro-coated channels or cavities are expected to possess enhanced thermal stability, higher catalytic activity, higher gas affinity and selectivity, and higher stability to oxidation and light.

In addition, fluorination may impart a variety of new functional properties to MOFs, such as superacidity, enhanced hydrophobicity, low surface energy and surface tension, low refractive index, exceptional chemical and biological inertness, and excellent optical and electrical properties. Many nano-scale fluorous environments have been created mainly via self-assembly processes, including nanoballs, channels, micelles, vesicles, microbubbles, tubules, and hollow fibers. However, porous FMOFs providing a fluorinated pore surface are yet unknown among the wide variety of MOFs.

Embodiments of the FMOFs of the present invention have both large channels and small cavities, both of which are capable of gas adsorption. The channels in representative embodiments of these FMOFs are open in direction of both the a- and b-crystallographic axes such that the gas adsorption sites are interpenetrating. Forming frameworks with narrow pores or cavities helps increase the binding energy of gases to the optimum range (about 15 kcal/mole) and thus facilitate $H_2$ adsorption at higher temperatures. Because the FMOFs, in certain embodiments, have multiple interacting channels and/or cavities whose walls can potentially interact with the same $H_2$ molecules, the sorption processes work cooperatively.

DETAILED DESCRIPTION OF PREFERRED EMBODIMENTS

Generally, the present invention relates to a class of neutral, extended nanotubular porous called "fluorinated metal-organic frameworks" ("FMOFs"), in which all the organic ligands are perfluorinated or partially fluorinated. The fluoro-lined cylindrical channels of the tubular frameworks possess hydrophobic internal cavities as a result of fluorination of all organic ligands.

Figure 1:
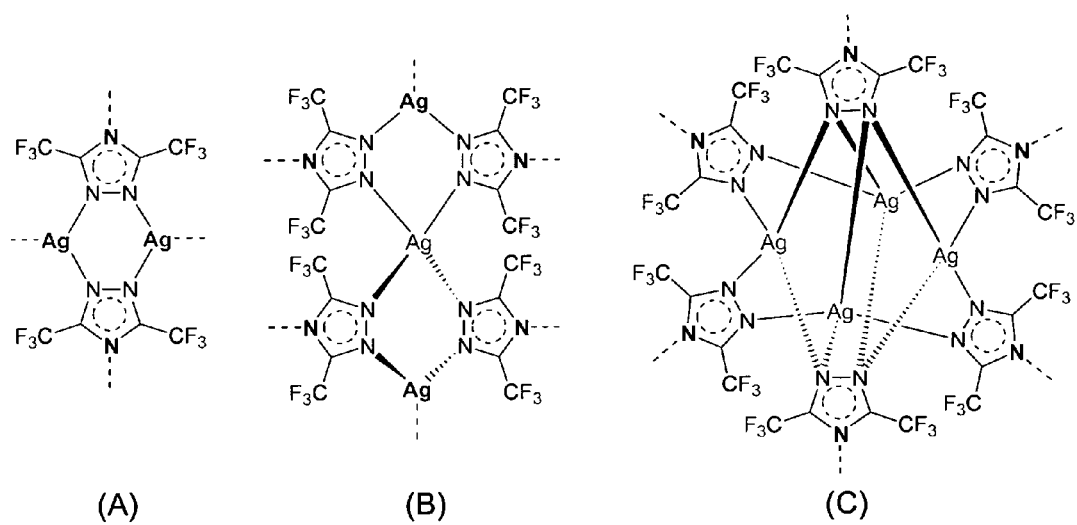
FIG. 1 shows the potential building blocks of silver(I)-triazolate clusters.

One embodiment of the present invention pertains to rigid, porous fluorous (i.e., perfluorinated) FMOFs with fluoro-lined channels that are capable of gas adsorption and desorption. All hydrogen atoms in the fluorous FMOFs have been substituted with fluorine atoms. One possible strategy for achieving these fluorous FMOFs uses robust, perfluorinated metal-triazolate clusters as building blocks, which consist of 4-coordinate tetranuclear clusters [$Ag_4L_6$] connected by 3-coordinate Ag(I) centers. Potential candidates for these building blocks include polynuclear silver(I)-triazolate clusters such as those shown in FIG. 1, which bear unsaturated metal sites or exo-N donor atoms; thus, they can readily assemble into coordination polymers with 1D chain, 2D sheet, or 3D framework structures.

Figure 2:
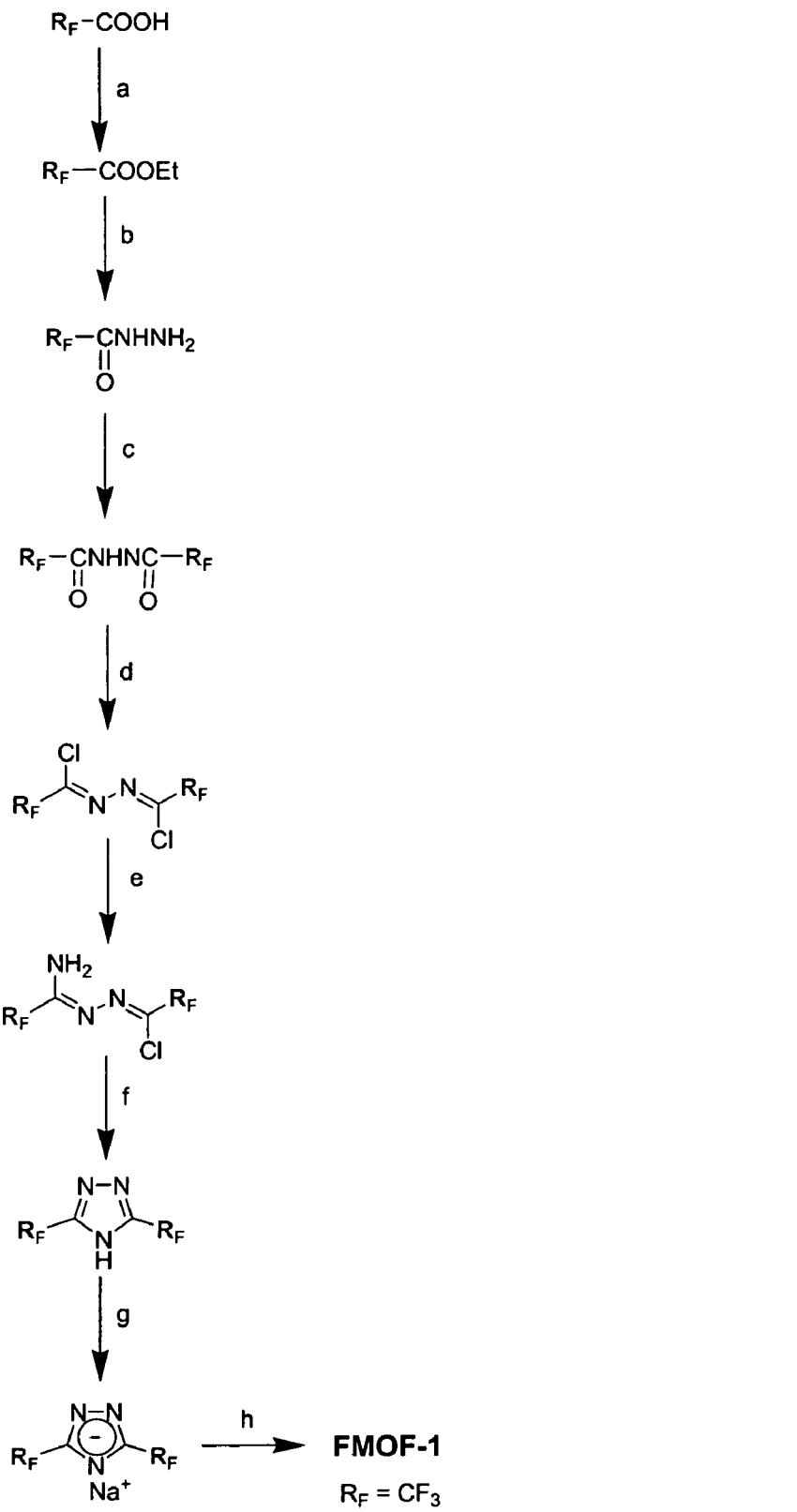
FIG. 2 shows a general synthetic scheme for selected embodiments of the fluorinated metal-organic frameworks ("FMOFs").

Synthesis of particular embodiments of the FMOFs utilizes the perfluorinated ligand 3,5-bis(trifluoromethyl)-1,2,4-triazole ("HL"). HL is synthesized from 2,5-dichloro-1,1,1,6,6,6-hexafluoro-3,4-diazahexa-2,4-diene (Abdul-Ghani, et al. 1995). HL then reacts with silver nitrate in methanol to afford colorless crystals upon evaporation and recrystallization from acetonitrile/toluene. A general synthetic scheme is illustrated in FIG. 2. In FIG. 2, the reagents used in different steps include: a. MeOH, $H_2SO_4$; b. $NH_2NH_2$; c. $R_F$—COCl; d. $POCl_3$; e. $NH_3$; f. $P_2O_5$; g. NaH; h. metal precursor ($AgNO_3$ for FMOF-1). $R_F$ represents fluorinated alkyl groups, e.g. $CF_3$, $CF_2CF_3$, $C_3F_7$, $C_4F_9$, $C_5F_{11}$, $C_6F_{13}$, $C_8F_{17}$, and such. Synthesis of specific compounds are described in the examples below. These examples and the general synthetic scheme can be used in the synthesis of other fluorinated triazole ligands and related fluorinated metal organic frameworks. For example, $R_F$ in FIG. 2 can have longer fluorinated alkyl groups or fluorinated aromatic groups.

Figure 3:
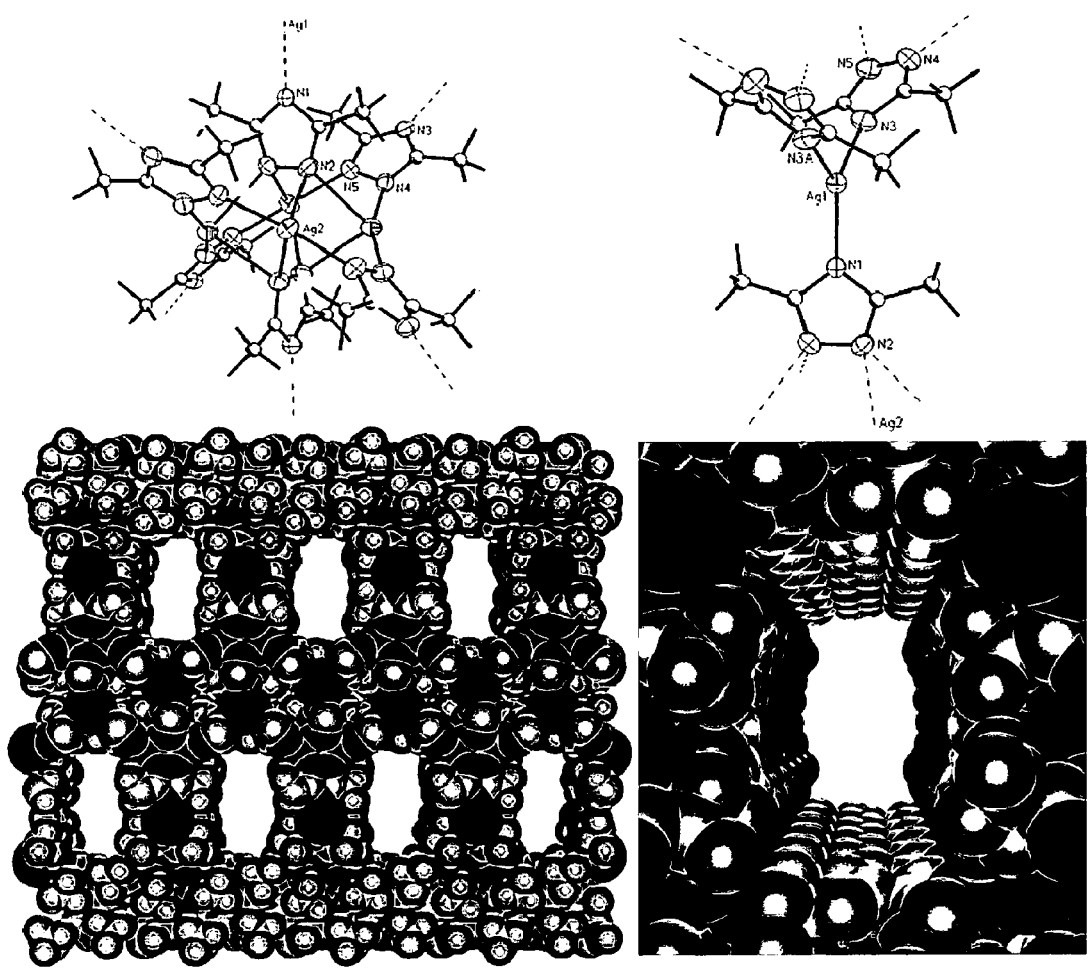
FIG. 3 shows the crystal structure of one embodiment, FMOF-1, at 100 K, with the top figures showing thermal ellipsoidal plots of the building blocks and the bottom figures showing space-filling representations of fluoro-lined 3D channels (left) and a view down one channel (right) of FMOF-1.

Analysis by X-ray crystallography revealed one embodiment, a neutral FMOF with the formula $\{Ag_2[Ag_4L_6]\}_n$, referred to as FMOF-1. The crystal structure of FMOF-1, shown in FIG. 3, shows extended 3D nanotubular open frameworks consisting of 6-connected tetranuclear [$Ag_4L_6$] clusters linked by 3-coordinate Ag(I) atoms. The crystal data for FMOF-1 are as follows: $C_{24}Ag_6F_{36}N_{18}$, FW=1871.64, Tetragonal, I −42d, a=13.3753(7) Å, c=39.281(4) Å, V=7027.2 (9) Å$^3$, Z=4, T=100 K, $D_c$=1.769 g/cm$^3$; $R_1$=0.0473, $wR_2$=0.1420, GOF=1.166.

FIG. 3 shows the structure of FMOF-1 at 100 K. The top figures show 50% thermal ellipsoidal plots of the building blocks, wherein six exo-N atoms of [$Ag_4L_6$] coordinate to six 3-coordinate Ag(I) centers. The lower figures show space-filling representations of the fluoro-lined 3D channels (left) and a view down one channel (right).

In FMOF-1, the six triazolate ligands utilize their 1- and 2-positioned N-atoms to link four 4-coordinate Ag(I) centers (Avg. Ag—N=2.20(1) Å and 2.64(1) Å for equatorial and axial bonds, respectively) into tetranuclear [$Ag_4L_6$] clusters (Ag . . . Ag=3.470(1) Å), which utilize their 4-positioned N-atoms to connect to one another via 3-coordinate Ag(I) centers (Avg. Ag—N=2.27(2) Å), generating a 3D framework of ($4^2$.6)($4^4$.$6^2$.$8^8$.10) topology. The framework can be viewed as consisting of open-ended, hollow tubes extending along the direction of both the a- and b-crystallographic axes with a crystallographically-imposed $S_4$ axis lying at the center of each channel. The cylindrical channels of the tubular framework possess hydrophobic internal cavities, as the $CF_3$ groups of the perfluorinated ligands point into the channels. A cross-section of each fluoro-lined channel in the space-filling representation also shown in FIG. 3 entails a semi-rectangular shape with 12×7.3 Å dimensions. These fluoro-lined channels account for 40.6% of the unit cell volume as calculated by PLATON (Spek, 2003), which is typical for high-porosity MOFs. Residual electron densities were too low (max=0.82e Å$^{-3}$) to locate possible solvent molecules in the cavities, so it is believed that the best structural refinement entails solvent-free channels. The channels entail hexagonal openings with an Ag . . . Ag distance of 18.7 Å for the longest diagonal of the non-planar 32-membered rings.

As shown in FIG. 3, in the embodiment referred to as FMOF-1, the silver atoms appear to be well protected under the fluorinated walls, imparting unusual air- and photo-stability despite the notoriety of Ag(I) species for being light sensitive. Indeed, FMOF-1 did not change when subjected to UV illumination in air for over 24 hours.

Packing diagrams for FMOF-1 crystals at 100 K show the hexagonal coordination geometry of the non-planar 32-membered rings. The structure can be obtained at room temperature after pretreatment of FMOF-1 to remove any solvent or gas molecules in the channels by heating the crystals at 100° C. in vacuum.

In addition, the structure of a pretreated single crystal of FMOF-1 was studied at 100 K. The resulting structure shows nitrogen molecules adsorbed in the open channels even though the only source of $N_2$ was the liquid nitrogen from the cryostream used for cooling the exposed crystal on the diffractometer (i.e., there was no high pressure of $N_2$ applied to a sealed sample). The adsorption of $N_2$ gas also appeared to occur not only in the large open channels but also in the small cavities. The structure shows 5.67 $N_2$ molecules per repeat unit.

A packing diagram for FMOF-1·toluene crystals at 100 K shows that crystals of FMOF-1 grown from toluene show a structure in which toluene molecules are adsorbed in the large open channels.

Figure 4:
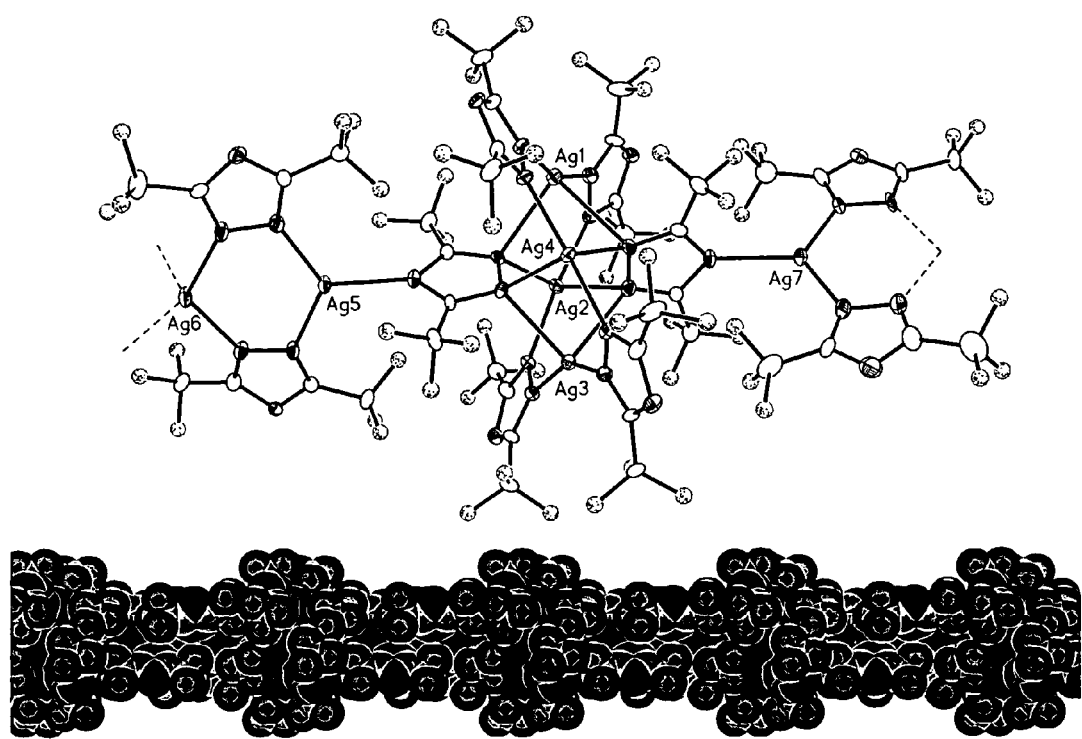
FIG. 4 shows a space-filling representation of one embodiment, FMOF-2, at 100 K.
Figure 5:
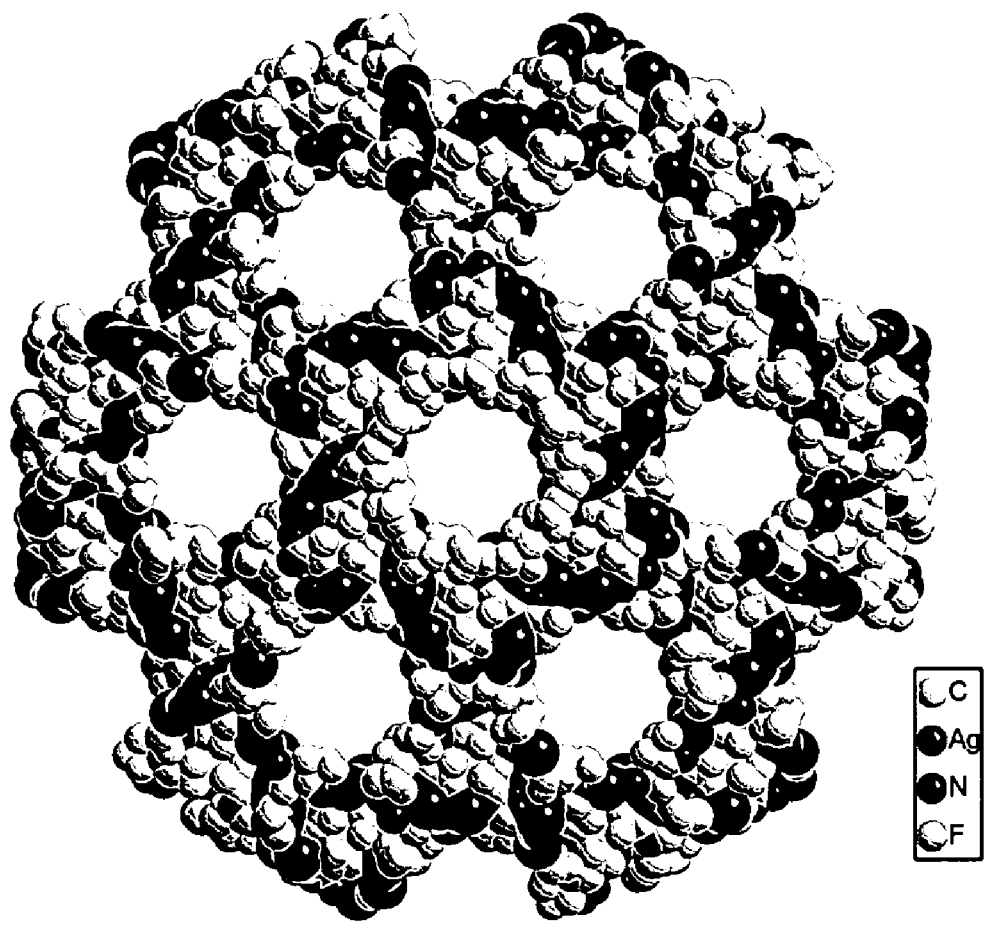
FIG. 5 shows a close-up view of a packing diagram of the solvent-containing structure of one embodiment, FMOF-2, at 100 K.

A further preferred embodiment of the present invention is referred to as FMOF-2. The FMOF-2 framework is a polymorphic form of the FMOF-1 framework with the same chemical composition of the metal and ligand but with a different packing arrangement of the 3-D supramolecular structure. FIG. 4 shows a space-filling representation of the FMOF-2 framework at 100 K while FIG. 5 shows a close-up view of the packing diagram for the solvent-containing structure at 100 K, which contains both open channels and cavities. The toluene molecules are lined in a well-organized facial arrangement with respect to the fluorinated walls of both the large channels and smaller cavities, underscoring the superacidity of these fluoro-lined channels and cavities.

Figure 6:
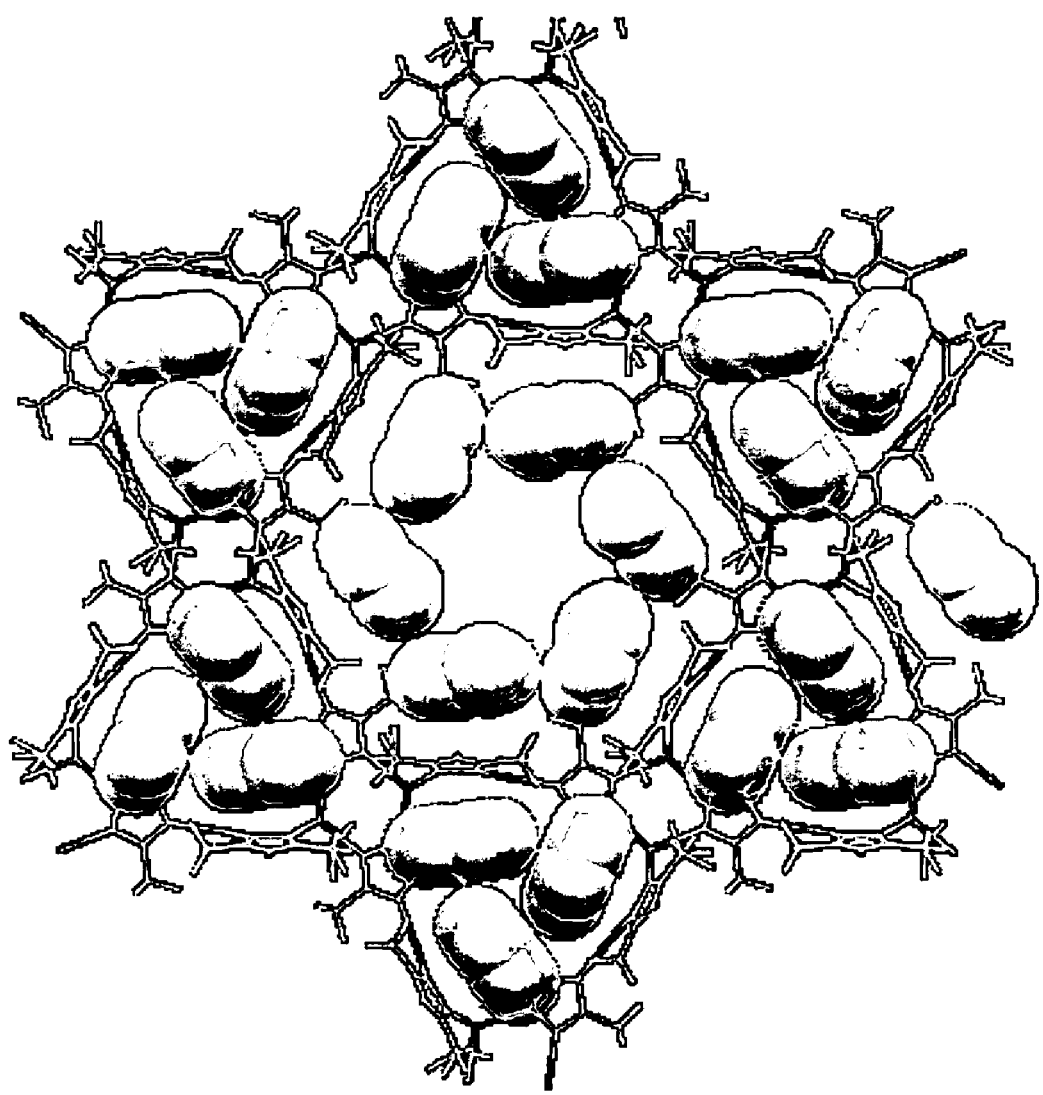
FIG. 6 shows a packing diagram for crystals of one embodiment, FMOF-3, at 100 K.

An additional preferred embodiment of the present invention is referred to as FMOF-3. The FMOF-3 framework is a polymorphic form of FMOF-1 and FMOF-2 frameworks but with a 2-D instead of 3-D supramolecular structure. FIG. 6 shows the packing diagram for FMOF-3 crystals at 100 K.

An additional preferred embodiment of the present invention is referred to as FMOF-4. The FMOF-4 framework is a polymorphic form of FMOF-1, FMOF-2, and FMOF-3. The packing diagram for FMOF-4 crystals at 100K shows that the structure of FMOF-4 is similar to FMOF-1 and FMOF-2 in that it is a 3-D framework while it is similar to FMOF-3 in that it contains only small cavities as opposed to large channels. Despite the latter, both FMOF-3 and FMOF-4 are useful for gas adsorption because gas molecules can indeed adsorb in small cavities.

The FMOFs exhibit many common properties, including solubility in many organic solvents, high thermal-, air-, and light-stability. The stability is likely imparted by the fluorous protection because of the known strength of the C—F bonds that line the channels and cavities as shown above for preferred fluorous embodiments. All FMOF materials can be considered as coated frameworks where the fluorous protection is an inherent part of the structure as opposed to being due to adding an external material. Another noteworthy property for FMOF materials is their high density (in the 1.6-2.2 g/mL range for select embodiments). This is extremely important for gas storage applications because it endows high volumetric capacity.

The FMOF materials contain open channels or cavities which can accommodate gas molecules at relatively high pressure and/or low temperatures to maximize their storage capacity. The gas molecules can then be released by decreasing the pressure and/or increasing the temperatures. The adsorption/desorption processes are usually reversible and can be fully controlled by pressure, temperature, or both. The quantity of $H_2$ will be very similar in adsorption and desorption points at similar pressures due to the reversibility of the process.

The FMOF materials of the current invention are not limited to the Ag(I)-triazolate embodiments shown above. Other porous Ag(I)-triazolates, as well as other metal-ligand combinations, are possible. Other metal components within the framework material can be used according to the present invention, including metal atoms of the main group, transition metal series, and lanthanide series of the periodic system of the elements. Among those metal components, particular examples include $Li^+$, $Na^+$, $K^+$, $Rb^+$, $Be^{2+}$, $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Pd^{2+}$, $Pd^0$, $Pt^{2+}$, $Pt^0$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$, $Bi^+$, and combinations thereof.

The ligands used for construction of the fluorinated MOFs are also not limited to fluorinated triazolates. Besides triazolates, any ligands with two or more donor atoms and two or more fluorine atoms can be used as bridging ligands for construction of fluorinated MOFs. With regard to construction of FMOFs, several other fluorinated organic ligands, such as fluorinated carboxylates, fluorinated polypyridines, fluorinated phosphines, fluorinated thiolates, and others, for coordination to various soft and hard metal centers, can also be used.

An important property of FMOFs is their large breathing capacity due to guest adsorption and/or temperature variation. FMOF embodiments have demonstrated gigantic negative thermal coefficient in presence or absence of guest molecules such as $N_2$.

Potential applications of the current FMOFs are wide-ranging and not limited to $H_2$ storage. Other examples include storage or transport of other gases, such as $CH_4$, $O_2$, $N_2$, CO, $CO_2$, $NO_x$, and vapors of hazardous organic solvents. These materials include fuel, greenhouse gases, and vapors of environmental pollutants and health hazards. The superior acidity and other structural factors discussed above regarding $H_2$ storage are also valid for these applications. Another example is gas separation, which is facilitated by the anticipated high selectivity of our fluorous materials. A further example is storage or separation of aromatic organic molecules, such as benzene, toluene, or xylenes. These are common carcinogens contained in gasoline, which are responsible for the warning signs usually posted on gas pumps. The affinity of the FMOF materials to these aromatic molecules is clearly illustrated by the toluene structures already discussed, particularly FIG. 5 for FMOF-2. An additional example is use in catalysis. The superior acidity, stability, open structures, and solubility of the FMOF materials are excellent features for use in multiple heterogeneous and homogeneous catalytic processes. Another application of the FMOFs is thermal expansion, including positive, negative, and zero thermal expansion materials.

Example 1

Gas Adsorption and Storage Capabilities

Figure 7:
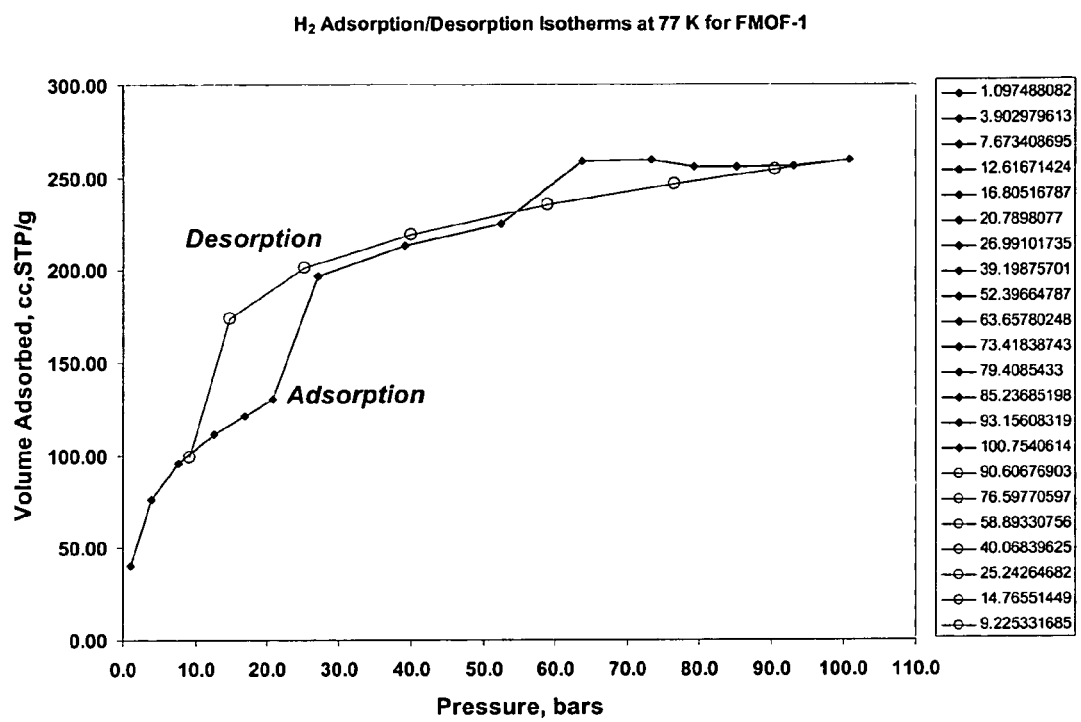
FIG. 7 shows the low-pressure $H_2$, $N_2$, and $O_2$ adsorption isotherms for the embodiment FMOF-1 at 77 K.

The high-pressure $H_2$ adsorption and desorption isotherms for the embodiment FMOF-1 were obtained at 77 K. These high-pressure data were obtained by VTI Corporation (Hialeah, Fla.) for the $H_2$ adsorption onto FMOF-1 up to ~100 bar and are shown in FIG. 7. Meanwhile, the low-pressure $H_2$, $N_2$, and $O_2$ adsorption isotherms for the embodiment FMOF-1 were also obtained at 77 K. These hydrogen, nitrogen, and oxygen adsorption data at pressures lower than 0.1 MPa (1 atm) were obtained by Micromeritics (Norcross, Ga.) measured with a standard static volumetric technique (Micromeritics® ASAP 2010). A sample holder configured to allow in-situ pretreatment in a flowing gas stream was used. Approximately 50-100 mg of sample was used for low-pressure isotherm measurements. The apparatus was calibrated for hydrogen measurements at 298 K using palladium powder. Hydrogen adsorption at pressures greater than 0.1 MPa and up to 10 MPa was also measured using a static volumetric technique. The non-ideality of hydrogen was accounted for by computing the compressibility factor using second and third virial coefficient correlations. Approximately 300 mg of sample was used for high-pressure isotherm measurements. All samples were pretreated in-situ to the measurement apparatus prior to isotherm measurements. The pretreatment conditions included degassing in vacuum at about 60° C. for a minimum of 1 hour. Ultra-high purity gases (99.999%) were used for all pretreatments and measurements. Molecular Sieve 3A purifiers were used on each gas stream to ensure purity was maintained throughout the experiments.

Table 1 below summarizes the gravimetric and volumetric storage capacity of FMOF-1 for hydrogen adsorption in comparison to representatives of the best metal-organic frameworks known to date and described in the indicated publications.

TABLE 1

| Sample (saturation pressure) | Gravimetric capacity (mg $H_2$/g) | Volumetric capacity (g $H_2$/L) | Notes |
|---|---|---|---|
| FMOF-1 (73.4 bar) | 23.4 | 41.3 | Pretreatment activation not optimized. |
| MOF-177 (68.5 bar) | 75.2 | 32.1 | Yaghi et al., *J. Am. Chem. Soc.* 2006, 128, 3494. |
| IRMOF20 (77.6 bar) | 66.7 | 34.1 | Yaghi et al., *J. Am. Chem. Soc.* 2006, 128, 3494. |
| Mn-BTT_1m' (90 bar) | 69.0 | 43.0 | Long et al., *J. Am. Chem. Soc.* 2006, 128, 16876. |

It is clear from Table 1 that the best metal-organic frameworks known previously have very low densities. Thus, their volumetric capacities are always lower than their gravimetric capacities. The opposite is true for the current FMOF materials. The high density of the FMOF materials (about 1.6-2.2 g/mL) is a noteworthy property. FMOF-1 shows a density of 1.77 g/mL, which gives rise to a higher volumetric capacity than its gravimetric capacity. Therefore, even without optimizing the pretreatment, FMOF-1 exhibits a very high volumetric capacity that is very similar to that of the best-performing reported MOFs in this particular parameter.

FMOF-1 also has both large and small cavities, both of which are capable of gas adsorption. Direct evidence of the influence of these on the $H_2$ adsorption process is shown in the data in FIG. 7, which clearly illustrate rises to multiple plateaus during the adsorption process. This unique and unusual behavior was reproduced by VTI for FMOF-1 to verify that the multiple curvatures are genuine. The four FMOF materials above illustrate a significant structural diversity in terms of channel size and interaction of adsorption sites. These aspects complement the high acidity and hydrophobicity of the open channels so as to increase the binding energy of $H_2$ and other gases to desired values for different applications.

In addition, FIG. 7 shows that the adsorbed gas molecules can be released by decreasing the pressure. The quantity of $H_2$ was very similar in adsorption and desorption points at similar pressures due to the reversibility of the process.

In general, FMOF-1 has large channels which accommodate gas molecules at low temperatures or/and at high pressure, and release the gas molecules at room temperature or/and under low pressure. Framework of FMOF-1 is stable and the gas adsorption process can be reproduced (recycled).

Other gases are also adsorbed effectively by the FMOF materials with various selectivity and sensitivity. Therefore, the invention is not limited to hydrogen adsorption by the FMOF materials. FIG. 7 shows that adsorption of nitrogen and oxygen is very high (higher than $H_2$ adsorption, which is a typical behavior of MOFs). The particularly high affinity to $O_2$ by the FMOFs in this invention is due to the fluorination because molecular materials are known to exhibit increased affinity to oxygen upon fluorination.

Example 2

Preparation of 1,2-bis(trifluoroacetyl)hydrazine

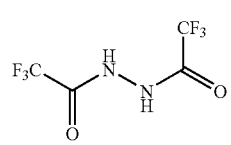

Trifluoroacetic acid (7.6 mL, 0.1 mol) was added to a stirred solution of trifluoroacethydrazide (12.8 g, 0.1 mol) in benzene (100 mL) and the mixture was heated under reflux for 2 h. A Dean and Stark trap was fitted, and reflux was continued for 3 h. Reflux was continued in the absence of the Dean and Stark trap (3 h) and then with the trap refitted (20 h). The resulting white solid was collected by filtration, dried in vacuum and identified as 1,2-bis(trifluoroacetyl)hydrazine (16.5 g, 73%). M.p. 173-175° C.

Example 3

Preparation of 2,5-dichloro-1,1,1,6,6,6-hexafluoro-3,4-diazahexa-2,4-diene

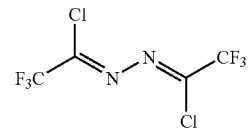

A mixture of N,N-diethylaniline hydrochloride (18.5 g, 0.1 mol), 1,2-bis(trifluoroacetyl)hydrazine (10.3 g, 0.46 mol) and phosphoryl chloride (160 mL) was stirred for 30 minutes under nitrogen in a flask fitted with a condenser leading to a cold trap (−78° C.). The mixture was heated under reflux for 5 h and then allowed to cool and stored overnight. The flask contents and the small amount of material which had condensed in the cold trap were combined and the two layers which had formed were separated. The layer was added to ice water (85 mL) and the mixture vigorously stirred for 1 h in a flask fitted with a condenser. Separation of the lower organic layer gave the main batch of the crude product (6.4 g). The original dark upper layer was treated similarly with ice water (75 mL) and the organic layer subjected to preliminary purification by trap-to-trap distillation in vacuum to afford a second batch of crude product (1.6 g). Distillation of the combined product through a vacuum-jacketed Vigreux column gave 2,5-dichloro-1,1,1,6,6,6-hexafluoro-3,4-diazahexa-2,4-diene (6.3 g, 53%) as an oil.

Example 4

Preparation of (ZZ)-1-amino-5-chloro-1,1,1,6,6,6-hexafluoro-3,4-diazahexa-2,4-diene

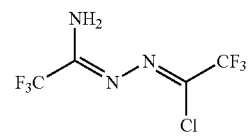

A solution containing aqueous ammonia (0.78 g, 45.9 mmol) in diethyl ether (30 mL) was added slowly over 1 h to a stirred solution of 2,5-dichloro-1,1,1,6,6,6-hexafluoro-3,4- diazahexa-2,4-diene (6.0 g, 23.0 mmol) in diethyl ether (60 mL) and water (30 mL) at 0° C., and stirring was continued for 3 h. The ether layer was separated, dried over $Na_2SO_4$ and the ether removed in vacuo to give (ZZ)-1-amino-5-chloro-1,1,1,6,6,6-hexafluoro-3,4-diazahexa-2,4-diene. Yield: 3.6 g (64%).

Example 5

Preparation of 3,5-bis(trifluoromethyl)-1H-1,2,4-triazole

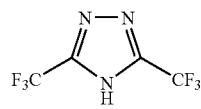

A solution of (ZZ)-1-amino-5-chloro-1,1,1,6,6,6-hexafluoro-3,4-diazahexa-2,4-diene (5.0 g, 20.7 mmol) in THF (20 mL) was heated under reflux for 3 days and the solvent was removed under reduced pressure to give a waxy solid. Purification by column (eluant: $CHCl_3$) affords 3,5-bis(trifluoromethyl)-1H-1,2,4-triazole as a colorless crystal. Yield: 1.0 g, 25%. M.p. 74-75° C.

Example 6

Preparation of sodium 3,5-bis(trifluoromethyl)-1,2,4-triazolate

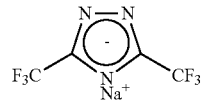

Sodium hydride (0.24 g, 0.01 mol) was added to 10 mL of anhydrous acetonitrile contained in a three-necked flask fitted with a nitrogen inlet, a dropping funnel and a condenser surmounted with a drying tube ($CaCl_2$). An equivalent amount of 3,5-bis(trifluoromethyl)-1H-1,2,4-triazole (2.0 g, 0.01 mmol) in 5.0 mL of anhydrous acetonitrile was added from the dropping funnel and the mixture stirred at room temperature for 24 h under a nitrogen atmosphere. Solvent was then removed in vacuo and the white residue of the sodium triazolide was used in the following reaction without separation.

Example 7

Preparation of FMOF-1 (FIG. 3)

$AgClO_4 \cdot H_2O$ (225 mg, 1.0 mmol) and the above sodium triazolide (250 mg, 1.1 mmol) in 30 mL of MeOH was stirred for 6 h and finally concentrated under reduced pressure to a small volume. Water was added to the residue and the precipitated colorless solid was filtered, washed with water and dried at 60° C. in vacuum to afford colorless crystalline solid. Recrystallization from acetonitrile-toluene afford colorless crystals of FMOF-1, yield: 153 mg (49%).

The procedures above can be generally used in the synthesis of other flourinated triazole ligands and related fluorous metal organic frameworks. For example, the $R_F$ in FIG. 2 can be replaced by longer flourinated alkyl groups or flourinated aromatic groups instead of $CF_3$.

REFERENCES CITED

The following publications are hereby incorporated by reference.

Other Publications

Abdul-Ghani, M. M.; Tipping, A. E. *J. Fluo. Chem.* 1995, 72, 95.
Long et al., *J. Am. Chem. Soc.* 2006, 128, 16876.
Ouellette, W.; Yu, M. H.; O'Connor, C. J.; Hagrman, D.; Zubieta, J. *Angew. Chem. Int. Ed.* 2006, 45, 3497.
Spek, A. L. *J. Appl. Crystallogr.* 2003, 36, 7.
Yang, G.; Raptis, R. G. *Chem. Commun.* 2004, 2058.
Yaghi, O. M.; Li, G. M.; Li, H. L. *Nature* 1995, 378, 703.
Yaghi et al., *J. Am. Chem. Soc.* 2006, 128, 3494.
Zhang, J. P.; Zhang, S. L. Huang, X.-C.; Chen, X.-M. *Angew. Chem. Int. Ed.* 2004, 43, 206.
Zhang, J. P.; Lin, Y.-Y.; Huang, X.-C.; Chen, X.-M. *J. Am. Chem. Soc.* 2005, 127, 5495.
Zhang, J. P.; Lin, Y.-Y.; Zhang, W.-X.; Chen, X.-M. *J. Am. Chem. Soc.* 2005, 127, 14162.

What is claimed is:

1. Fluorinated metal-organic frameworks, comprising
   a plurality of metal clusters, wherein the metal clusters comprise Ag(I); and
   a plurality of linking ligands, wherein the linking ligands comprise triazolates,
   wherein the linking ligands connect adjacent metal clusters to form a coordination polymer, wherein hydrogen atoms are substituted completely by fluorine atoms in each ligand, and wherein the fluorinated metal-organic frameworks have 3-D, 2-D, or 1-D structures.

2. The fluorinated metal-organic frameworks of claim 1, wherein the clusters are assembled into coordination polymers having a plurality of open-ended, hollow channels and internal cavities with hydrophobic internal areas.

3. The fluorinated metal-organic frameworks of claim 2, wherein the open-ended, hollow channels and internal cavities are free of solvent molecules.

4. The fluorinated metal-organic frameworks of claim 2, wherein the open-ended, hollow channels and internal cavities are capable of adsorbing and desorbing gases.

5. The fluorinated metal-organic frameworks of claim 1, wherein the fluorinated metal-organic frameworks are capable of adsorbing gases.

6. The fluorinated metal-organic frameworks of claim 5, wherein the gases are hydrogen, methane, oxygen, nitrogen, carbon monoxide, carbon dioxide, nitric oxide, nitrous oxide, or vapors of hazardous organic solvents.

7. The fluorinated metal-organic frameworks of claim 5, wherein the gases are adsorbed by increasing pressure and/or decreasing temperature.

8. The fluorinated metal-organic frameworks of claim 1, wherein the fluorinated metal-organic frameworks are capable of adsorbing aromatic organic molecules.

9. The fluorinated metal-organic frameworks of claim 8, wherein the aromatic organic molecules are benzene, toluene, or xylenes.

10. The fluorinated metal-organic frameworks of claim 1, wherein the fluorinated metal-organic frameworks are capable of desorbing gases.

11. The fluorinated metal-organic frameworks of claim 10, wherein the gases are desorbed by decreasing pressure and/or increasing temperature.

12. The fluorinated metal-organic frameworks of claim 1, wherein the fluorinated metal-organic frameworks have densities in the range of about 1.6 g/mL to about 2.2 g/mL.

13. The fluorinated metal-organic frameworks of claim 1, wherein the fluorinated metal-organic frameworks have volumetric storage capacities for gases that exceeds their gravimetric storage capacities for gases.

14. The fluorinated metal-organic frameworks of claim 1, wherein the fluorinated metal-organic frameworks have negative, positive, or zero thermal expansion in presence or absence of gas molecules.

15. A method for the adsorption and storage of gases or aromatic organic molecules, comprising exposure of the gases or aromatic organic molecules to the fluorinated metal-organic frameworks of claim 1.

16. A storage device for gases or aromatic organic molecules, comprising the fluorinated metal-organic frameworks of claim 1.

17. The fluorous metal-organic frameworks of claim 1, wherein the coordination polymer comprises perfluorinated polynuclear Ag(I)-triazolate clusters.

* * * * *